United States Patent
Rawson et al.

(10) Patent No.: US 7,132,078 B2
(45) Date of Patent: Nov. 7, 2006

(54) ASSAY APPARATUS

(75) Inventors: Keith Rawson, Ely (GB); Michael Thomas Pearson, West Molesey (GB); Nicholas David Long, Hampton (GB)

(73) Assignee: Cambridge Life Sciences PLC, Ely (GB)

( * ) Notice: Subject to any disclaimer, the term of this patent is extended or adjusted under 35 U.S.C. 154(b) by 712 days.

(21) Appl. No.: 10/333,779

(22) PCT Filed: Jul. 27, 2001

(86) PCT No.: PCT/EP01/08724

§ 371 (c)(1),
(2), (4) Date: May 23, 2003

(87) PCT Pub. No.: WO02/10754

PCT Pub. Date: Feb. 7, 2002

(65) Prior Publication Data

US 2003/0180815 A1   Sep. 25, 2003

(30) Foreign Application Priority Data

Jul. 31, 2000   (GB) ................................ 0018741.9

(51) Int. Cl.
   *G01N 21/00* (2006.01)
   *G01N 31/22* (2006.01)

(52) U.S. Cl. .................... 422/58; 422/55; 422/56; 422/68.1; 422/70; 436/529; 436/164; 436/169; 435/283.1; 435/287.6; 435/287.2; 435/287.7; 435/288.7

(58) Field of Classification Search .............. 422/50, 422/55, 56, 57, 58, 61, 68.1, 69, 70, 82.05; 436/518, 530, 528, 529, 164, 166, 169, 172; 435/283.1, 287.1, 287.2, 287.6, 287.7, 288.7

See application file for complete search history.

(56) References Cited

U.S. PATENT DOCUMENTS

| 4,632,901 | A |   | 12/1986 | Valkirs et al. |
|-----------|---|---|---------|----------------|
| 4,857,453 | A | * | 8/1989  | Ullman et al. ............. 435/7.92 |
| 5,096,669 | A | * | 3/1992  | Lauks et al. ........... 204/403.02 |
| 5,413,761 | A | * | 5/1995  | Dulaney ...................... 422/56 |
| 5,424,035 | A | * | 6/1995  | Hones et al. .................. 422/55 |
| 5,635,358 | A |   | 6/1997  | Wilding et al. |
| 5,726,010 | A | * | 3/1998  | Clark ............................ 435/5 |
| 5,744,096 | A | * | 4/1998  | Jones et al. .................... 422/58 |
| 5,756,362 | A |   | 5/1998  | Durst et al. |
| 6,017,494 | A | * | 1/2000  | Ashihara et al. ............. 422/58 |
| 6,300,141 | B1| * | 10/2001 | Segal et al. ............. 435/287.1 |

(Continued)

FOREIGN PATENT DOCUMENTS

WO    WO 88/08534    11/1988

(Continued)

Primary Examiner—Long V. Le
Assistant Examiner—Melanie J. Yu
(74) Attorney, Agent, or Firm—Nath & Associates PLLC; Joshua B. Goldberg; Sheldon M. McGee (57) ABSTRACT

Assay apparatus comprising: a moulded cartridge containing a lateral flow test strip which has a label pad containing an enzyme antibody or antigen conjugate having affinity for an analyte; a capture zone having a capture antibody or antigen having affinity for said analyte; a reagent storage blister; a means for removing sample and/or label pad from the lateral flow test strip; a meter in which the cartridge is inserted enabling the control for reagent release from the reagent storage blister and for the sample and/or label pad removal and a means of providing quantitative measurement of said analyte.

17 Claims, 4 Drawing Sheets

U.S. PATENT DOCUMENTS

| | | | |
|---|---|---|---|
| 6,607,922 B1 * | 8/2003 | LaBorde | 436/514 |
| 6,977,173 B1 * | 12/2005 | Chandler | 435/287.1 |
| 2003/0049849 A1 * | 3/2003 | Mori et al. | 436/46 |
| 2003/0170881 A1 * | 9/2003 | Davis et al. | 435/287.2 |

FOREIGN PATENT DOCUMENTS

| | | |
|---|---|---|
| WO | WO 96/15454 | 5/1996 |
| WO | WO 02/10754 | 2/2002 |

* cited by examiner

ASSAY APPARATUS

TECHNICAL FIELD

This invention relates to assay apparatus. Particular embodiments of the invention relate to assay apparatus, which provides a quantitative measurement of the amount of analytes that are contained in a biological sample such as blood or urine, for example. More specifically, the invention relates to enzyme substrate and/or wash delivery in one step immunoassays. Another embodiment of the invention relates to assay apparatus, which provides a quantitative measurement of analytes that are contained in environmental samples, such as pesticides in river water for example.

PRIOR ART

There are many assay devices available commercially which are intended as quick sample tests for detecting and measuring environmental and biologically relevant compounds, including metabolites, hormones, toxins and pathogen derived antigens. Typically such assays are based on specific binding reactions and therefore use sensitive reagents such as antibodies.

One type of immunoassay utilizes a flow-through device, which is described in U.S. Pat. No. 4,632,901. This device comprises a membrane or filter to which antibody is bound. An absorbent material in contact with the membrane or filter induces flow therethrough when a fluid sample is added to the membrane or filter. A fluid sample is applied to the membrane and, if the target antigen is present, is bound by the antibody. A solution of labelled antibody is then added followed by a washing step to remove unbound-labelled antibody. The presence of labelled antibody on the membrane after washing indicates the presence of the antigen in the sample being assayed.

Another type of immunoassay utilizes a lateral flow device which is described in WO 88/08534 'Immunoassays and devices therefor'. This refers to a device comprising a dry porous carrier which communicates directly or indirectly with the exterior of the casing such that a liquid test sample can be applied to the porous carrier, the device also containing a labelled specific binding reagent for an analyte which labelled specific binding reagent is freely mobile within the porous carrier when in the moist state, and unlabelled specific binding reagent for the same analyte which unlabelled reagent is permanently immobilised in the detection zone on the carrier material and is therefore not mobile in the moist state, the relative positioning of the unlabelled reagent and detection zone being such that liquid sample applied to the device can pick up labelled reagent and thereafter permeate into the detection zone, and the device incorporating means enabling the extent (if any) to which the labelled reagent becomes in the detection zone to be observed.

A principle advantage of the lateral flow immunoassay is the ease with which the testing procedure is carried out. These so called 'one step' immunoassays, whether they be flow-through or lateral flow constructs, have inherent limitation to the use as true one step quantitative immunoassays in that where the label is an enzyme, (as enzyme labelled antibody or enzyme labelled antigen) it must be kept separate from its substrate until separation of bound and free enzyme label is complete. Furthermore, with currently available designs, it is impractical to perform washing steps, which are frequently desirable to improve sensitivity and decrease background readings. Wash steps normally involve a second operation by the user and may lead to error where time delays or no wash are performed.

DESCRIPTION OF INVENTION

The present invention is concerned with adapting and improving the known techniques, such as those referred to above, to provide diagnostic test devices which are quick, reliable, quantitative and which only require sample addition.

In accordance with an aspect of the invention, there is provided assay apparatus comprising: an assay cartridge which is protective and functional having one port for receiving a liquid sample and guiding fluid flow of the sample to contact the lateral flow immunoassay test strip at the sample pad. The cartridge also contains a reagent storage blister and mechanism for releasing solution on to the lateral flow immunoassay test strip. The lateral flow immunoassay test strip within the cartridge comprises of the sample pad which serves to begin the flow of analyte containing sample, and will be constructed of a bibulous material that exhibits low analyte retention. The sample pad also functions as mechanical filter, entrapping red blood cells and undesirable particles present in the sample. A label pad is then provided containing an enzyme-antibody conjugate having affinity for an analyte is in fluid communication with the sample pad and capture zone. The capture zone contains a capture antibody having affinity for the analyte immobilised on a membrane and is in fluid communication with an absorbent pad which removes excess liquid. The cartridge also contains two sets of electrodes, one carbon interdigitated pair covered by an enteric polymer coating and the other a pair of silver contacts. The carbon electrodes are in direct contact with the capture zone and the silver electrodes are placed just before the absorbent pad on the membrane. Another set of polymer coated carbon electrodes maybe placed on the absorbent pad to measure the activity of the enzyme-antibody conjugate. The assay apparatus also comprises of a meter into which said assay cartridge is inserted. The meter provides electronic support for the electrodes enabling a quantitated result to be displayed. On insertion of the cartridge in to the meter, the reagent storage blister is pierced allowing substrate to flow into a substrate pad associated with the reagent storage blister. The sample is added to the port in the assay cartridge once the cartridge is fully inserted into the meter. The sample flows through the sample pad, label pad and membrane until the fluid makes contact with the silver electrodes. This creates a circuit which releases a plunger in the meter onto an activating arm mounted in the assay cartridge. The activating arm is forced against the reagent storage blister bringing the substrate pad into contact with the membrane just after the label pad. At the same time the activating arm pushes the label and sample pads, disconnecting them from the membrane and stopping further flow of sample. The substrate solution acts as a wash solution until sample flow is stopped when the absorbent pad is full. The silver electrodes measure the change in conductance from the substrate solution and indicate that the wash is good and can calculate the flow rate of the strip by timing the change in conductance. This adds an extra level of control for the device. The analyte/enzyme-antibody conjugate captured on the capture zone reacts with the substrate released into the membrane causing the dissolution of the polymer membrane on the carbon electrode. This results in a change in capacitance which is directly proportional to the amount of enzyme-antibody conjugate captured and hence analyte concentration.

Preferably, said result provides a quantitative measurement of the amount of said analyte contained in said patient sample.

More preferably, the apparatus comprises means for releasing a solution of substrate onto said lateral flow immunoassay test strip which reacts with said conjugate to produce an indicator detectable by said detector.

Preferably said indicator causes the pH of said solution to increase, said signal being representative of the increase in capacitance.

The solution releasing means may comprise means defining a storage cavity; a cover for said cavity, and piercing means integral with said cavity-defining means for piercing said cover. Alternatively, the solution releasing means may comprise means defining a storage cavity; a cover for said cavity, and piercing means external to said cavity defining means operable to drive the cavity defining means to reduce the volume of the cavity and to cause the cover to be pierced.

Preferably said detector comprises a pair of electrodes. Preferably, the meter comprises means for driving said releasing means into abutment with said test strip. Preferably, the driving means is controlled by said control means. Preferably, said driving means is operable to cause the cover of said releasing means to be pierced. Preferably, said driving means is operable to separate said first pad from said strip.

Most preferably, the driving means is simultaneously operable to drive said releasing means into abutment with said substrate, to cause the cover of said releasing means to be pierced and to separate said sample pad from said strip.

The lateral flow immunoassay test strip, reagent storage blister and detector may be provided within a cartridge which comprises a disposable component of said assay apparatus. Preferably, said cartridge is insertable into a meter, which contains said control means.

Preferably, said cartridge includes a sample insertion aperture which is normally closed by a movable door, said door being opened automatically to allow the insertion of a patient sample upon insertion of said disposable cartridge into said meter.

A further aspect of the invention provides a method of detecting the presence of a sample; introducing a wash reagent and stopping further sample addition by removal of sample and/or label pad; measuring the flow rate of the device and calculating effective washing; and measuring the enzyme activity to account and re-calibrate for variation due to temperature or stability, for example.

Embodiments of the invention will now be described by way of example only with reference to the accompanying drawings, in which.

The constituent components of the assay apparatus of embodiments of the invention will now be described with reference to the accompanying drawings. Operation of the apparatus will not be described with reference to the use of the apparatus for any particular type of testing. However, it will be appreciated that the apparatus may be used for a variety of different tests, and thus it should be noted that the embodiments of the invention described herein should not be construed as being limited to any particular type of testing.

Figure 1:
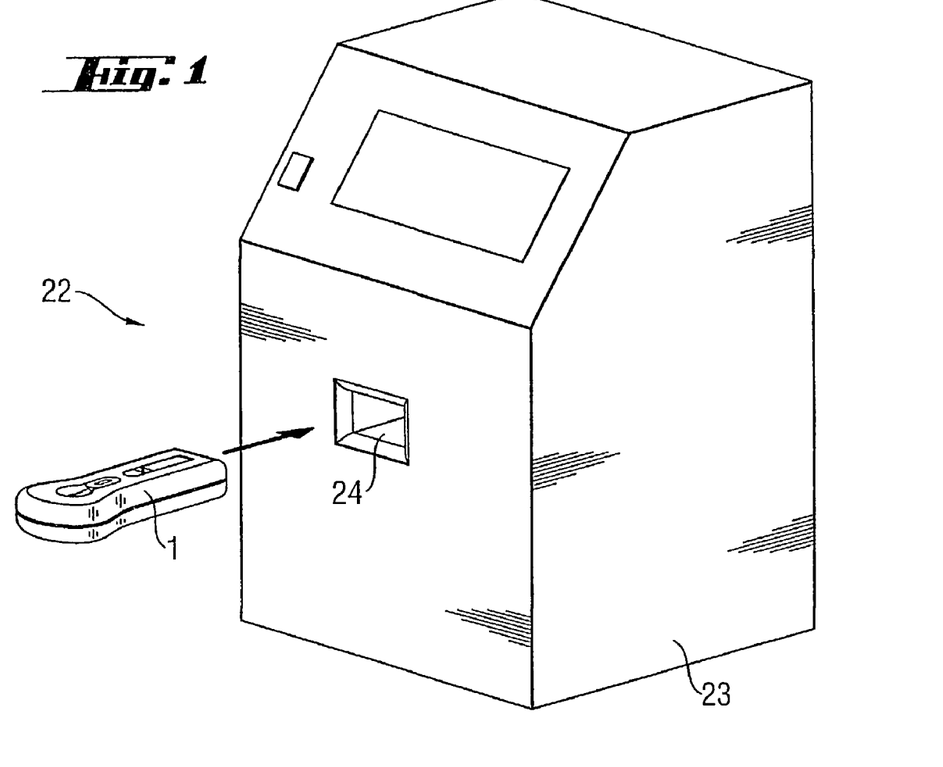
FIG. 1 is a schematic representation of another embodiment of assay apparatus.
Figure 2:
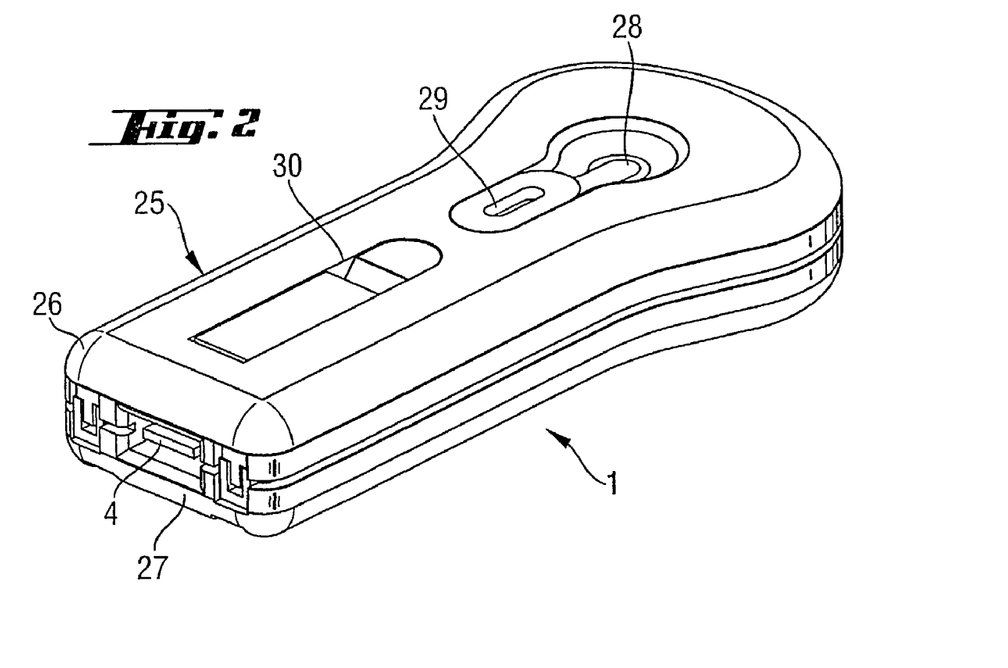
FIG. 2 is a schematic perspective view of a component of FIG. 1.

As shown in FIG. 1, the assay apparatus 22 comprises a disposable assay cartridge 1 and a meter 23 into which the disposable assay cartridge 1 may be inserted through a slot 24 when it is desired to test a patient sample. The disposable assay cartridge includes equivalent components to the base, strip, electrode, lower arm, reagent storage blister, upper arm and cover plate of FIG. 3. The meter 23 includes control electronics, drive aim and actuating solenoid FIG. 2 is a schematic perspective view of an illustrative assay cartridge for use with the apparatus of FIG. 1. As shown the assay cartridge 1 comprises an outer casing 25, which is formed in two parts, an moulded upper part 26 and a lower moulded part 27 which are snapped together. The upper part 26 is formed with a sample insertion aperture 28, which is normally closed—when the assay cartridge is not inserted in the meter 23—by a movable door 29. The upper part 26 of the casing 25 is also formed with a second aperture 30 by means of which the drive arm of the meter 23 can penetrate the interior of the assay cartridge 25. The movable door 29 also normally closes the second aperture 30.

Figure 3:
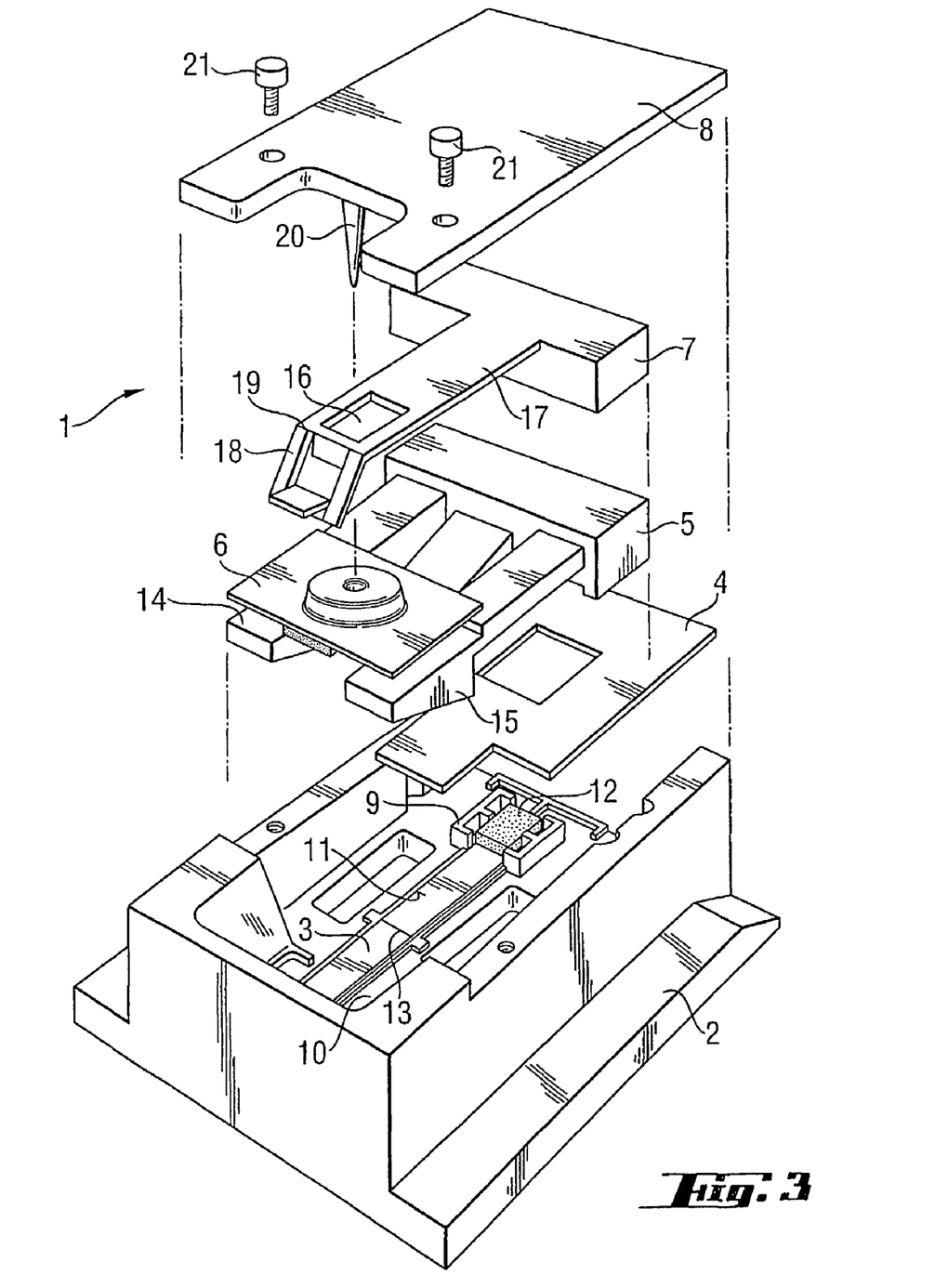
FIG. 3 is an exploded view of part of one embodiment of assay cartridge.
Figure 3A:
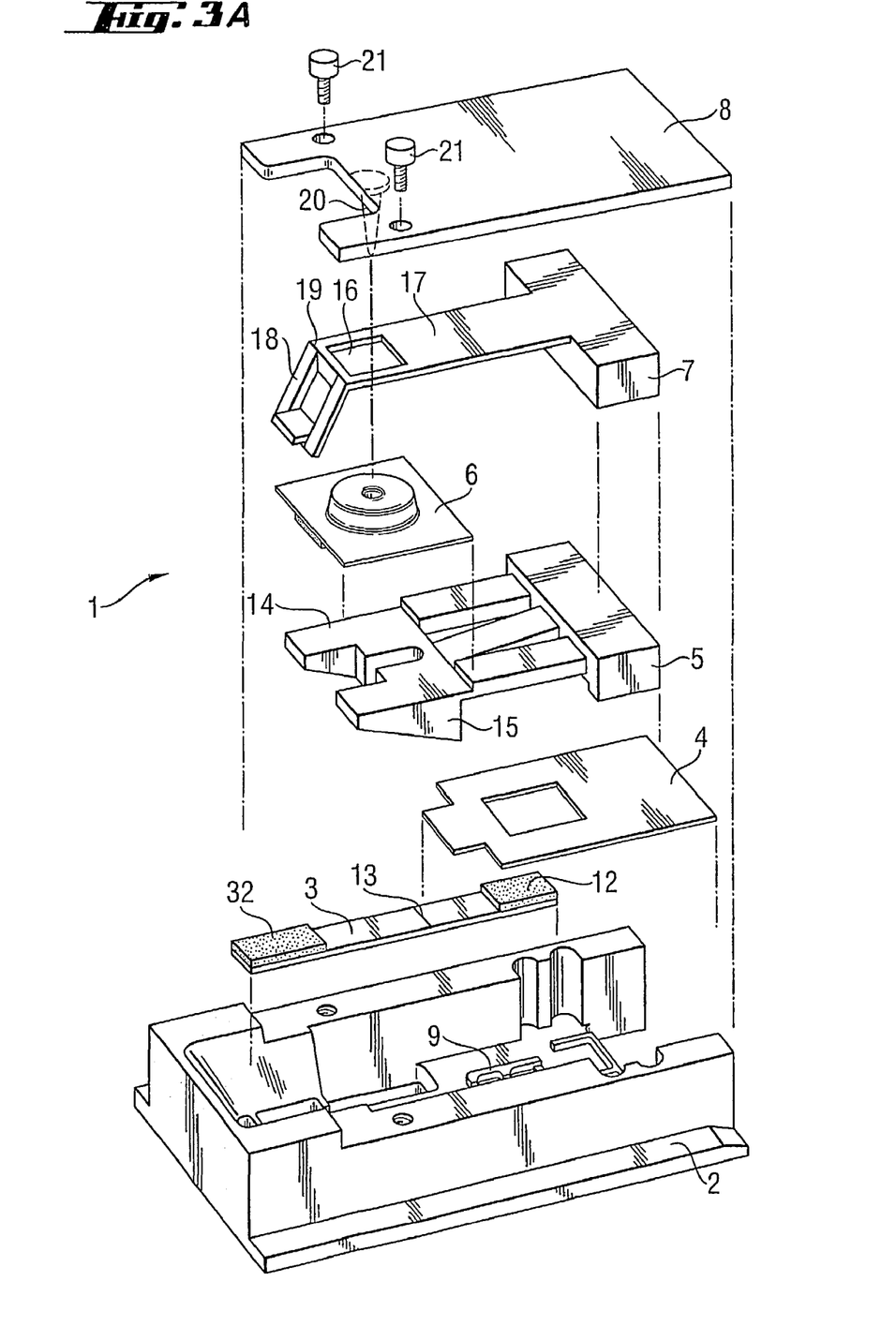

FIG. 3 is an exploded schematic view of part of an assay cartridge according to an embodiment of the invention. As shown, the cartridge 1 comprises a base 2 on which the lateral flow immunoassay test strip 3 is mounted, the electrode 4, a lower arm 5, and the reagent storage blister 6, an upper arm 7 and a cover plate 8.

The base 2 is formed with upstanding walls 9 in a floor portion 10 thereof which define a cavity 11 in which the lateral flow immunoassay test strip 3 is received. The electrode 4 is fitted over the lateral flow immunoassay test strip 3 so that the absorbent pad 12 of the lateral flow immunoassay test strip 3 may protrude through a possible cut-out in the electrode 4. The electrode may also cover the absorbent pad. When fitted over the lateral flow immunoassay test strip 3, the electrodes face the upper surface of the lateral flow immunoassay test strip 3 so that the electrode extends to the capture region 13 of the lateral flow immunoassay test strip 3 and the second electrode is located proximate the absorbent pad 12. A third electrode maybe located on the absorbent pad 12.

The lower arm 5 is rested on the electrode 4 and is provided with a shelf portion 14 on which the reagent storage blister may be mounted. A pair of ramps 15 is provided in this embodiment on the underside of the lower arm 5 (although they need not be provided in other embodiments) and the function of these ramps will later be described.

The reagent storage blister 6 is placed on the lower arm shelf 14 once the lower arm has been rested on the electrode 4, and the upper arm 7 is fitted over the reagent storage blister 6 and rested on the lower arm 5 so that the reagent storage blister 6 is sandwiched between the upper and lower arms. The upper arm 7 is placed so that a hole 16 in an elongate portion 17 thereof roughly overlies the reagent storage blister, and so that an actuating arm portion 18 fixed to the elongate portion 17 by a hinge 19 extends beyond the reagent storage blister 6.

The cover 8 may then be located over the above mentioned components so that a spike 20 extending from the underside of the cover protrudes through the hole 16 of the elongate portion 17 of the upper arm 7 and engages with the reagent storage blister 6. Once the above components have been correctly located, the cover may then be attached to sidewalls of the base 2 by screws 21. Tightening the screws 21 causes the ramps 15 on the underside of the lower arm 5 to abut against the floor portion 10 of the base to drive the reagent storage blister 6 towards the spike 20. The assay cartridge is then ready to be inserted into the meter and accept a patient sample.

When a patient sample is placed on the sample pad, red blood cells are retained and plasma flows through. The target analyte in the sample binds with a labelled antibody impregnated in the label pad, and the labelled target analyte flows along the strip 3 (along with the remainder of the sample) towards the absorbent pad 12. As the labelled target analyte passes through the region 13 of the strip 3 impregnated with a capture antibody, the labelled target analyte binds with the capture antibody and is retained in the region 13 of the strip 3. The remainder (or at least a substantial proportion thereof) of the sample flows to the end of the strip 3 and into the absorbent pad (sink) 12 fixed thereto.

As the sample flows into the absorbent pad 12, the electrode contacts on 4 detect a change in conductance and the control electronics determines that the sample has flowed through the strip 3. The control electronics then triggers the solenoid to release the drive arm (which in this embodiment is spring driven) so that the drive arm engages with and drives the upper arm 7—in the region of the hinge 19—towards the floor portion 10 of the base 2.

As the upper arm is driven towards the floor portion 10, the actuating portion 18 is driven outwards to straighten the upper arm 7. As the actuating portion 18 is driven outwards it engages with the sample and label pad and scrapes the sample and label pad away from and out of contact with the strip 3 so as to cut off the supply of sample to the strip. Simultaneously, driving the upper arm towards the floor portion 10 of the base 2 causes the reagent storage blister 6, and in particular the substrate pad (which by now will be laden with fluid from within the reagent storage blister cavity) of the reagent storage blister, to be driven into abutment with the strip 3. As the substrate pad is driven into abutment with the strip 3, fluid from the pad flows from the substrate pad along the strip 3 to wash any unbound sample and conjugate from the region 13 of the strip 3 towards the absorbent pad 12. As the solution passes through the region 13 of the strip 3, the substrate solution reacts with the bound labelled target analyte to produce a detectable product.

As the substrate solution removes the sample from the strip 3 to the absorbent pad 12, the control electronics via the electrodes on 4 detect a change in conductance which signifies that the sample has been effectively washed from the strip. At this point the meter then determines with the polymer coated electrodes on 4 the increase in capacitance of the region 13 of the strip—the change in capacitance being directly related to the quantity of bound labelled target analyte, and thus to the quantity of target analyte in the patient sample. The capacitance may then be displayed to the person operating the apparatus via suitable display means, or alternatively the capacitance sensed may be tallied in a preprogrammed calibration data with an "amount of target analyte" value and the amount value may then be displayed to the user.

Once the capacitance change has been sensed and the results displayed typically within 10 minutes, the testing procedure for that sample is complete, and the cartridge 1 discarded.

Figures 4, 5:
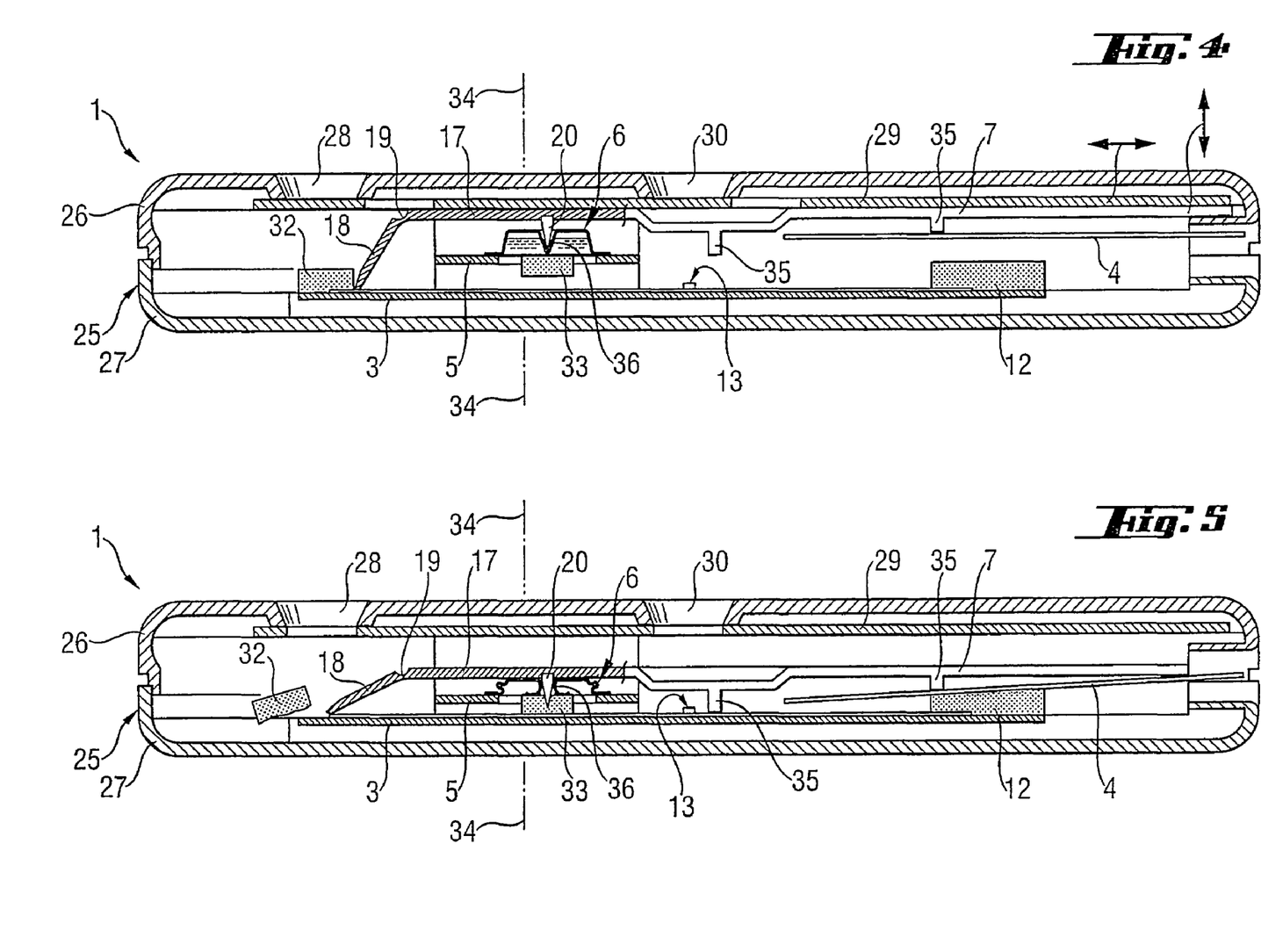
FIG. 4 is a cross-sectional view of the component of FIG. 3 in a starting configuration.
FIG. 5 is a cross-sectional view of the component of FIG. 3 in a finishing configuration.

FIG. 4 is a cross-sectional view of the cartridge 1 shown in FIG. 2 prior to insertion into the meter 23. As shown, within the upper 26 and lower 27 parts of the cartridge 1 (which together form the cartridge casing 25), a strip 3 such as that shown in FIG. 3 is provided. A reagent storage blister 6 is mounted above the strip 3 on a flexible mount 5. An actuating arm 7 is provided, and the arm 7 is maybe formed with a spike 20, which engages with the reagent storage blister 6. The arm 7 is also provided with an actuating portion 18, which abuts, against the sample/label pad 32 of the strip 3, and pillars 35 on actuating arm 7, which abut an electrode 4. As shown, one end of the electrode 4 protrudes from the casing 25 so that the electrode can be engaged with the control electronics within the meter 23, when the cartridge is inserted into the meter slot 24.

Upon insertion of the cartridge 1 into the meter 23, the door 29 is lockingly engaged with drive arms (not shown) within the meter 23 and driven towards the left hand side of FIG. 4 to open the sample insertion aperture 28 and the second aperture 30. Advantageously, the drive arms (not shown) remain engaged with the door 29 so that when the cartridge 1 is withdrawn from the meter, the door 29 is pulled towards the right hand side of FIG. 4 to close the sample insertion aperture 28 and the second aperture 30.

FIG. 5 is a cross sectional view of the cartridge 1 after it has been inserted into the meter slot 24, and after the drive arm within the meter 23 has been driven into abutment with the arm 7 to cause the arm spike 20 to drive the blister spike 36 within the reagent storage blister to pierce its foil cover. As the arm is driven to cause piercing of the foil cover, it simultaneously causes the first and second electrode contacts to be driven into contact with the strip 3, the pad 33 on the reagent storage blister 6 to be driven to abut the strip 3, and the arm actuating portion 18 to remove the sample/label pad 32 from the strip.

In use, the cartridge 1 in the state illustrated in FIG. 4 is inserted into the slot 24 of the meter 23, whereupon the door 29 is driven to open the sample insertion aperture and the second aperture. When fully inserted into the meter, all of the cartridge from the exposed electrode end up to the line 34 on FIGS. 4 and 5 will be enclosed within the meter.

At this point, a patient sample may be dropped through the sample insertion aperture 28 and onto the sample pad 32 of the strip 3. Components of the sample bind with a labelled antibody impregnated in the label pad, and the resulting labelled target analyte flows together with the remainder of the sample along the strip towards the absorbent pad 12 and through the region 13 of the strip where the labelled target analyte is restrained by a capture antibody impregnated in this region 13 of the strip 3.

When the fluid reaches the second set of electrodes on 4, the control electronics releases the solenoid (not shown) to release the driven arm which drives through the open second aperture 30 and drives the arm 7 to push the first electrodes into abutment with the strip, the spike 20 to pierce the foil cover, the pad 33 into abutment with the strip 3 and the actuating arm portion 18 to remove the sample/label pad 32. Substrate fluid from the pad 33 then flows along the strip 3 to wash unbound sample to the absorbent pad 12 (and to initiate a reaction in the region 13 of the strip 3 which produces a detectable product) where a change in conductance is sensed by the second electrodes on 4 which causes the control electronics to measure the capacitance at the polymer coated electrodes on 4 in abutment with the strip region 13, and from this to generate a result indicative of the amount of target analyte in the patient sample. Withdrawing the cartridge 1 from the meter 23 causes the door 29 to be closed, whereupon the cartridge may be safely discarded. The meter is then ready for testing of a new patient sample with a new cartridge 1.

It will be understood that embodiments of the invention have been described herein by way of example only and further that modifications may be made within the scope of the claims. For example, whilst the cartridge of FIG. 4 employs an electrode 4 having polymer coated electrode for sensing for an analyte, it will be apparent an optical testing system (or any other system) could instead be employed in dependence upon the marker used to mark the antibody impregnated in the sample/label pad 32 and effective ways to detect the presence of that marker, for example by absorbance, fluorescence or chemiluminescence. The label pad could contain gold or coloured latex particles conjugated to an antibody or antigen so that the detection is based on the measurement of reflectance.

In another example, the cartridge of FIG. 2 could also house the electronics for controlling the measurement, driving the activating arm and releasing the reagent storage blister solution. The cartridge may have a read out to display the quantitative result or write the data to an integral detachable microchip for external analysis.

The invention claimed is:

1. An assay apparatus comprising: a moulded cartridge containing a lateral flow test strip which has a sample/label pad containing an enzyme antibody or antigen conjugate having affinity for an analyte; a capture zone having a capture antibody or antigen having affinity for said analyte; a reagent storage blister comprising a solution; a means for removing said sample/label pad from the lateral flow test strip and for piercing said reagent storage blister; a detector for providing quantitative measurement of said analyte; a meter in which the cartridge is inserted enabling control for reagent release from the storage blister, the sample/label pad removal, and providing quantitative measurement of said analyte.

2. The apparatus according to claim 1, wherein said quantitative measurement provides an amount of said analyte contained in said biological sample.

3. The apparatus according to claim 1, wherein said reagent storage blister contains a substrate for said enzyme antibody or antigen conjugate that can also act as a wash solution for the lateral flow test strip.

4. The apparatus according to claim 1, wherein said means of providing quantitative measurement is via said enzyme antibody or antigen conjugate that reacts with the substrate to produce a product that can be detected electrochemically using electrodes within the cartridge that are in contact with the lateral flow test strip.

5. The apparatus according to claim 1, further comprising an electrode within the cartridge, wherein said electrode detects fluid flow in the lateral test strip and thereby triggers the means for piercing the reagent blister, thereby releasing the solution from the reagent blister and removing the sample/label pad from the lateral flow test strip.

6. The apparatus according to claim 1, further comprising an electrode within the cartridge, wherein said electrode detects fluid flow in the lateral test strip and measures a change in conductance of the solution from the reagent blister thereby calculating flow rate and confirming effective washing of the lateral flow test strip.

7. The apparatus according to claim 1, wherein said means for removing said sample/label pad from the lateral flow test strip and for piercing said reagent storage blister is an operating arm that is operable to separate said sample/label pad from the lateral flow test strip thereby stopping a sample and/or conjugate from entering the lateral flow test strip.

8. The apparatus according to claim 1, wherein said means for removing said sample/label pad from the lateral flow test strip and for piercing said reagent storage blister is an activating arm that is operable to cause a cover of the reagent blister to be pierced and to cause abutment of said reagent storage blister with the lateral flow test strip to allow fluid to enter the lateral flow test strip.

9. The apparatus according to claim 1, further comprising a means of providing control measurement of an additional enzyme antibody or antigen conjugate in the absorbent pad with a substrate to produce a product that can be detected electrochemically using electrodes within the cartridge that are in contact with the absorbent pad in the lateral flow test strip and thereby correct the quantitative measurement of the analyte due to variations in enzyme activity.

10. The apparatus according to claim 1, wherein said means of providing quantitative measurement is via said enzyme antibody or antigen conjugate that reacts with the substrate to product a product that is detected optically using a detector that is contained in the meter and measures changes in either reflectance, absorbance, fluorescence or chemiluminescence.

11. The apparatus according to claim 5, wherein said electrode is polymer coated and measures changes in capacitance of said product due to an amount of analyte on the capture zone of the lateral flow test strip.

12. The apparatus according to claim 1, wherein said reagent storage blister comprises a means for defining a storage cavity, a cover for said cavity, and said piercing means are located internal or external to said cavity defining means operable to drive the cavity defining means to reduce the volume of the cavity and to cause the cover to be pierced.

13. The apparatus according to claim 1, wherein said substrate and said detector for providing quantitative measurement are provided within said cartridge which comprises a disposable component of said assay apparatus.

14. The apparatus according to claim 13, wherein said cartridge is insertable into said meter which contains said control means.

15. The apparatus according to claim 14, wherein said cartridge includes a sample insertion aperture which is normally closed by a movable door being opened automatically to allow insertion of a patient sample upon insertion of said disposable cartridge into said meter.

16. A method of quantitatively measuring an analyte comprising providing the assay apparatus of claim 1, placing a patient sample on the sample/label pad of said apparatus and obtaining a quantitative measurement of said analyte.

17. A method of detecting the presence of a substance in a sample comprising providing the assay apparatus of claim 1, placing a patient sample on the sample/label pad of said apparatus and detecting whether a substance is present in said sample.

* * * * *

UNITED STATES PATENT AND TRADEMARK OFFICE
CERTIFICATE OF CORRECTION

PATENT NO. : 7,132,078 B2  Page 1 of 1
APPLICATION NO. : 10/333779
DATED : November 7, 2006
INVENTOR(S) : Rawson et al.

It is certified that error appears in the above-identified patent and that said Letters Patent is hereby corrected as shown below:

Claim 4, Column 7, Line 42,
Please delete " the substrate "
and
replace with
-- a substrate --

Claim 9, Column 8, Line 13,
Please delete " an additional "
and
replace with
-- said --

Signed and Sealed this

First Day of January, 2008

JON W. DUDAS
*Director of the United States Patent and Trademark Office*